US006689067B2

(12) United States Patent
Sauer et al.

(10) Patent No.: US 6,689,067 B2
(45) Date of Patent: Feb. 10, 2004

(54) METHOD AND APPARATUS FOR ULTRASOUND GUIDANCE OF NEEDLE BIOPSIES

(75) Inventors: Frank Sauer, Princeton, NJ (US); Gianluca Paladini, Princeton, NJ (US); Ali Khamene, Plainsboro, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 0 days.

(21) Appl. No.: 10/304,427

(22) Filed: Nov. 26, 2002

(65) Prior Publication Data

US 2003/0120154 A1 Jun. 26, 2003

Related U.S. Application Data

(60) Provisional application No. 60/339,151, filed on Nov. 28, 2001.

(51) Int. Cl.$^7$ ................................................. A61B 8/14
(52) U.S. Cl. ........................ 600/464; 600/461; 600/437; 606/130; 601/2
(58) Field of Search ................................. 600/407–472; 606/130; 601/2–4

(56) References Cited

U.S. PATENT DOCUMENTS

| | | | | |
|---|---|---|---|---|
| 4,484,569 A | * | 11/1984 | Driller et al. | 600/439 |
| 4,527,569 A | * | 7/1985 | Kolb | 600/461 |
| 4,651,732 A | * | 3/1987 | Frederick | 606/130 |
| 4,763,662 A | * | 8/1988 | Yokoi | 600/461 |
| 4,848,569 A | * | 7/1989 | Leishman | 206/365 |
| 4,932,414 A | * | 6/1990 | Coleman et al. | 600/445 |
| 5,056,917 A | * | 10/1991 | Nowacki et al. | 356/124 |
| 5,316,014 A | * | 5/1994 | Livingston | 600/567 |
| 5,647,373 A | * | 7/1997 | Paltieli | 600/567 |
| 5,810,841 A | * | 9/1998 | McNeirney et al. | 606/130 |
| 6,030,348 A | * | 2/2000 | Unger et al. | 600/564 |
| 6,096,049 A | * | 8/2000 | McNeirney et al. | 606/130 |
| 6,110,112 A | * | 8/2000 | Heywang-Koebrunner | 600/439 |
| 6,146,390 A | * | 11/2000 | Heilbrun et al. | 606/130 |
| 6,206,890 B1 | * | 3/2001 | Truwit | 606/130 |
| 6,216,029 B1 | * | 4/2001 | Paltieli | 600/427 |
| 2003/0038112 | * | 2/2003 | Paladini et al. | 600/439 |

* cited by examiner

*Primary Examiner*—Dennis W. Ruhl
*Assistant Examiner*—William C. Jung (57) ABSTRACT

An ultrasound scanning system having an ultrasound transducer (10) which provides ultrasound images (33), a computer to process the ultrasound information and to render the ultrasound image (33) correctly positioned and scaled for display on a flat panel monitor (29) which has a display size similar to the actual physical size of the ultrasound image (33). A half silvered mirror (30) redirects the image (33) so that the user (32) perceives the image (33) as if it occupied the actual physical location of the structures (34, 35) appearing in the image (33). An illumination (22) unit projects onto a patient (13) a line of light (3) that is within the imaging plane (4) projected by the ultrasound transducer (10) into the patient (13). Alternatively a video camera may be used to display a guide line (15) that is coplanar with the imaging plane (4). A mechanical mount (16) combines the transducer (10), monitor (29), mirror (30), and source of illumination (22) or video camera in a correct geometrical alignment.

20 Claims, 6 Drawing Sheets

METHOD AND APPARATUS FOR ULTRASOUND GUIDANCE OF NEEDLE BIOPSIES

CLAIM OF PRIORITY

The present patent application is based on and claims priority from Provisional U.S. Patent Application No. 60/339,151 of the same title filed on Nov. 28, 2001.

RELATED APPLICATIONS

The present application is related to U.S. patent application Ser. No. 10/202,352 [2001P13330 US 01], filed Jul. 24, 2002, and entitled OPTICAL NEEDLE GUIDE FOR ULTRASOUND GUIDED NEEDLE BIOPSY and U.S. patent application Ser. No. 10/222,170 [2001 P 15267 US 01], filed Aug. 16, 2002, and entitled VIDEO-ASSISTANCE FOR ULTRASOUND GUIDED NEEDLE BIOPSY, both of which are incorporated by reference herein.

BACKGROUND

1. Field of the Invention

This invention relates to generally to a method and apparatus for manipulating needle-like medical instruments such as performing ultrasound guided needle biopsies and similar ultrasound guided procedures.

2. Discussion of the Related Art

Needle-like instruments are often used in medical procedures, and must be manipulated accurately. For example, in a needle biopsy, the needle has to be inserted into an anatomical target to remove a tissue sample. Ultrasound guidance is routinely used for example, when performing breast needle biopsies. The real time ultrasound images allow the physician to locate the target and to monitor the needle position. An example of a typical ultrasound imaging apparatus is disclosed in U.S. Pat. No. 5,503,152, entitled ULTRASOUND TRANSDUCER ASSEMBLY AND METHOD FOR THREE DIMENSIONAL IMAGING, issued on Apr. 2, 1996 to Oakley, et al.

The biopsy procedure is usually performed within the projected ultrasound image plane. With the ultrasound transducer being in a position where the target is visible in the displayed ultrasound image, the insertion point of the needle is ideally chosen so that the point resides along a line residing at the intersection of the projected ultrasound plane and the patient's skin surface. The needle is then preferably oriented so that it lies within this plane and points towards the target. When the needle is inserted it will appear in the ultrasound image, and the progress of the needle along a path towards the target can be visually monitored.

One difficulty inherent with performing an ultrasound guided needle biopsy is to correctly position and orient the needle so that the needle resides within the same plane as the displayed ultrasound image. Mechanical needle guides are commercially available to facilitate this task. They are clipped onto the transducer and constrain the movement of the needle so that it is forced to stay in a plane aligned with the transducer. Examples of such mechanical guides are disclosed in U.S. Pat. No. 5,076,279 entitled NEEDLE GUIDE FOR ASSEMBLY UPON AN ULTRASOUND IMAGING TRANSDUCER, issued to Arenson et al. on Dec. 31, 1991 and U.S. Pat. No. 6,475,152 entitled BIOPSY NEEDLE GUIDE FOR ATTACHMENT TO AN ULTRASOUND TRANSDUCER, issued on Nov. 5, 2002 to Kelly, Jr. et al. Even though the needle can be reliably placed in the plane of the ultrasound image, many physicians find the rigid constraint imposed by the use of a mechanical guide bothersome and consequently do not use one. Physicians typically want to be able to make corrective adjustments to the path of the needle as it approaches the target, which is not easily achieved with the constraints of the mechanical needle guide. In addition, because a mechanical guide constrains the needle entry point to be close to the transducer, it is not possible to insert the needle at the distance from the transducer, as is required for shallow needle angles.

Whether or not the physician is utilizing a mechanical guide, she must look away from the patient at the ultrasound image display and manipulate the needle without direct reference to either her hand or the target. This causes an unnatural eye hand coordination problem that creates additional complications for the physician performing the procedure. Ideally, the physician would be able to look directly at the desired path and destination point of the needle, but the opacity of the human body normally prevents such a view.

One technology that provides a simulated view inside the body during the performance of a needle biopsy is Real Time Tomographic Reflection. A discussion of this technique is provided in REAL TIME TOMOGRAPHIC REFLECTION: PHANTOMS FOR CALIBRATION AND BIOPSY by George Stetten et al., Proceedings IEEE and ACM International Symposium on Augmented Reality, 29–30 October 2001, N.Y. City, N.Y., pages 11–19. In this technique, the ultrasound image is visually merged with the normal exterior view of the patient. The physician's hands and the needle appear in the physician's natural field of view while the biopsy is being performed.

SUMMARY OF THE INVENTION

A guide according to principles of the present invention utilizes a light beam or video camera as a guide for placing the needle in the ultrasound plane. In one embodiment, the present invention includes an optical guide for a needle-like instrument comprising an ultrasonic transducer that projects a planar ultrasound beam into an imaging plane beneath a surface and a source of illumination, aligned with the ultrasonic transducer. The source of illumination projects a light beam onto the surface, the light beam being coplanar with the imaging plane. A viewing device, displays an image produced by the ultrasonic transducer which appears to be superimposed on the surface while the light beam is visible on the surface. The line of light on the patient's skin marks the intersection of the ultrasound plane with the patient's skin surface and hence marks the location of possible in-plane entry points for the needle. The user places the tip of the needle on the line of light projected onto the skin. Then the needle is oriented. When the needle is aligned in an in-plane pose, the needle is seen to be illuminated by the light along its length. The image displayed on the viewing device provides guidance to adjust the tilt of the needle within the ultrasound plane towards the target.

In a different embodiment of the present invention, the light beam is replaced by a video camera. An apparatus for video assisted guidance of a biopsy needle comprises means for projecting an ultrasonic imaging plane beneath a surface, means for creating a video image of the surface, and means for inserting graphic markers on the video image of the surface. The inserted graphic markers are substantially coplanar with the ultrasonic imaging plane. By looking at the image, the physician may place the needle on the skin along the superimposed line, and then orient the needle to be co-linear with the line. The viewing device generates a composite image containing the image produced by the ultrasonic transducer and the image of the surface along with the graphic markers.

DETAILED DESCRIPTION

Figure 1:
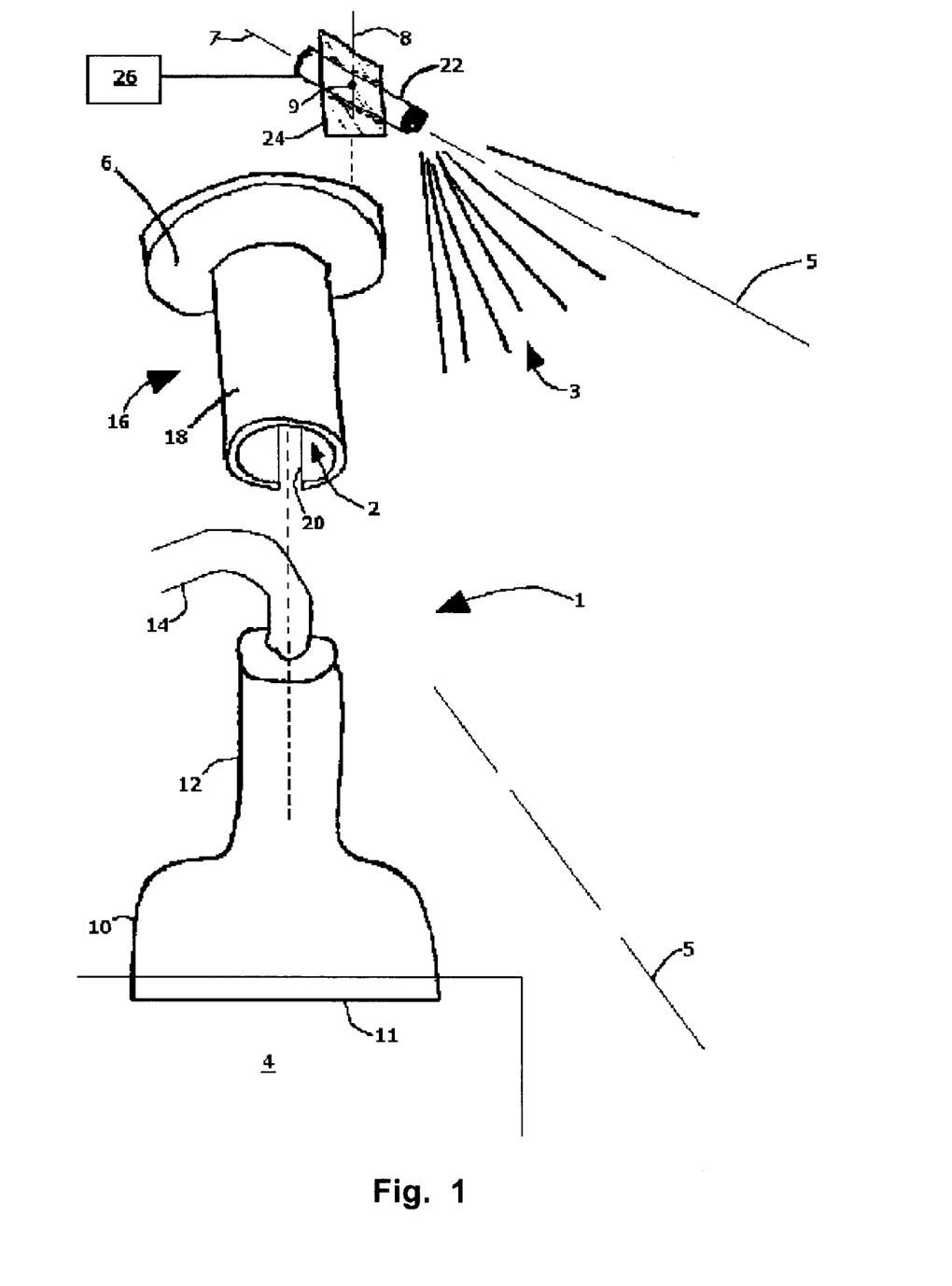
FIG. 1 is an exploded view of a first embodiment of an ultrasonic transducer and optical guide constructed according to the principles of the present invention.
Figure 2:
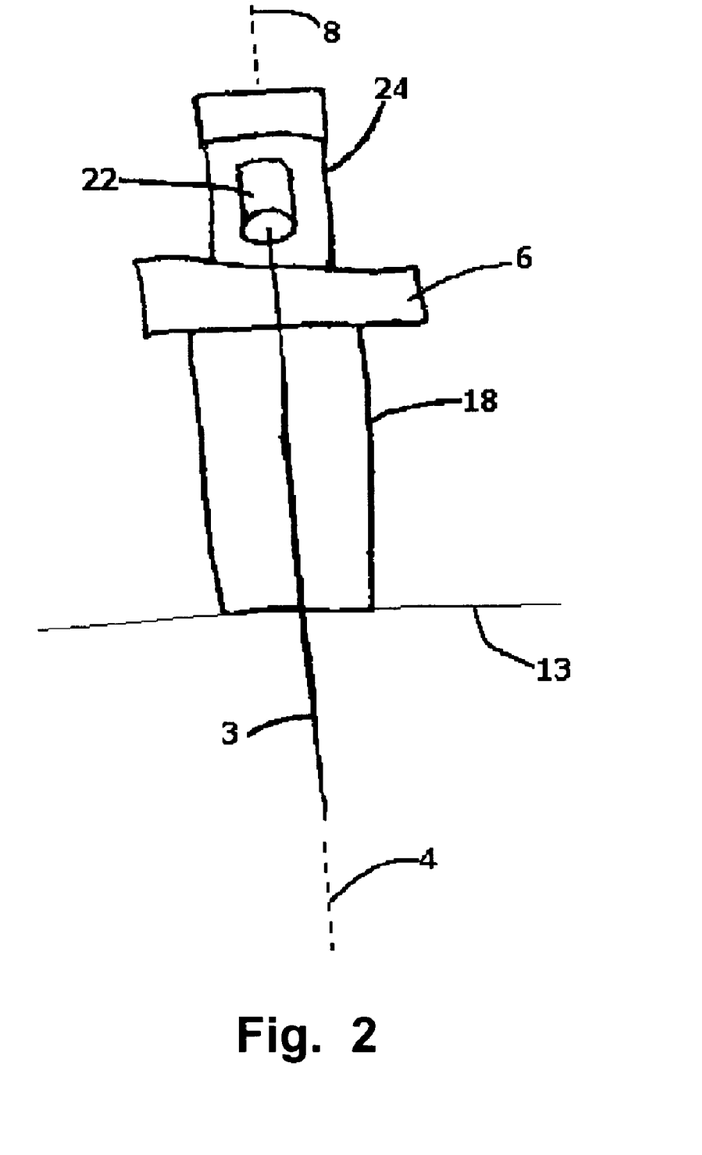
FIG. 2 is an elevation view of the assembled transducer and optical guide depicted in FIG. 1.
Figure 7:
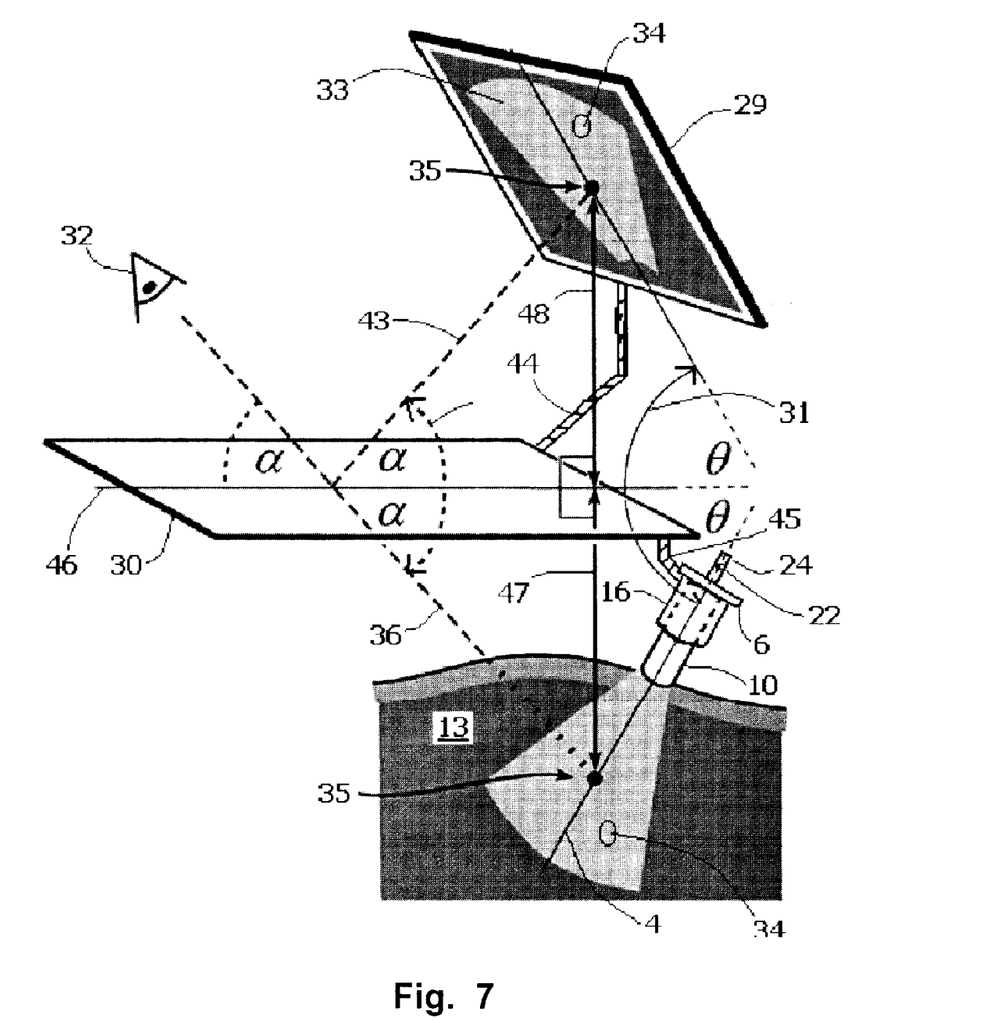
FIG. 7 is a pictorial representation of an ultrasound guidance apparatus constructed according to the principles of the present invention.

Referring to FIGS. 1, 2 and 7, the transducer and optical guide assembly 1 of the present invention is seen to include an ultrasonic transducer 10 capable of transmitting a planar ultrasonic beam into an imaging plane within a human body and receiving the reflected sonic energy for further image processing. The transducer 10 includes a handle 12 that is gripped the operator's hand during use in order to position the transducer so as to ultrasonically illuminate the area of interest in the patient 13. A cable 14 extends from the handle 12 and supplies a path for power and data transmission to and from transducer 10. The transducer 10 projects an imaging plane 4 of ultrasonic energy. The ultrasound plane or ultrasound imaging plane 4 denotes the plane, determined by the pose and geometry of the ultrasound transducer 10, in which the ultrasound imaging system collects image data.

A mounting unit 16 includes a platform portion 6 connected to a cylindrical portion 18. Mounting unit 16 may be an integrally formed unitary piece or it may be fabricated by joining separate parts that form platform portion 6 and cylindrical portion 18. The cylindrical portion 18 includes a slot 20 sufficiently wide to allow passage of cable 14 into at least some part of the interior 2 of cylindrical portion 18. Mounting unit 16 is placed onto the handle 12 of transducer 10 by slipping the cylindrical portion 18 over and onto the handle 12. Being essentially in the form of a hollow cylinder adapted to fit over the handle 12, mounting unit 16 may be made of any convenient and suitable material such as metal or plastic.

Rigidly affixed to the platform portion 6 is a light mount 24. A light source 22 is secured within the mount 24 which permits adjustment of the light source 22 about vertical axis 8 and lateral axis 9. Suitable adjustment of the mount 24 causes light source 22 to project its beam 3 in a desired direction. Preferably the light source 22 is a laser, such as the laser diode module L54-17, manufactured by the Edmund Scientific Company located at 60 Pearce Avenue, Tonawanda, N.Y. 14150-6711. The light source 22 is powered by power supply 26.

The beam 3 projected by a laser will be a relatively thin line 5 that defines and is collinear with the longitudinal axis 7 of the light source 22. The light source 22 is mounted to platform portion 6 and adjusted so that the projected laser beam 5 is coplanar with the ultrasound imaging plane 4. The operator of the unit 1 grips the cylindrical portion 18 and places the surface 11 of transducer 10 against the patient's body 13. The platform portion 6 serves as a stop or brace for the operator's hand. The transducer 10 projects ultrasonic imaging plane 4 into the patient 13. The laser beam 3 that resides within the imaging plane 4 is projected onto some portion of the patient's skin and creates a line visible to the operator 32. Since the operator 32 wishes to place a needle into the patient so that it will reside within the imaging plane 4, the portion of beam 3 visible on the patient's skin will define a series of points at which the needle should enter the skin.

Once the tip of the needle is placed on the patient's skin somewhere along the beam 3, the needle itself is manipulated by the user so that it is also aligned with the beam 3, and therefore with the imaging plane 4. The user can see this as a reflection of the light beam 3 off the surface of the needle. When the needle is placed on the appropriate place on the patient's skin, and aligned with the light beam 3 properly, it will stay in the imaging plane 4 of the ultrasonic transducer, and remain visible in the ultrasonic image. The needle may then be inserted to the desired location to take the biopsy sample.

Figure 3:
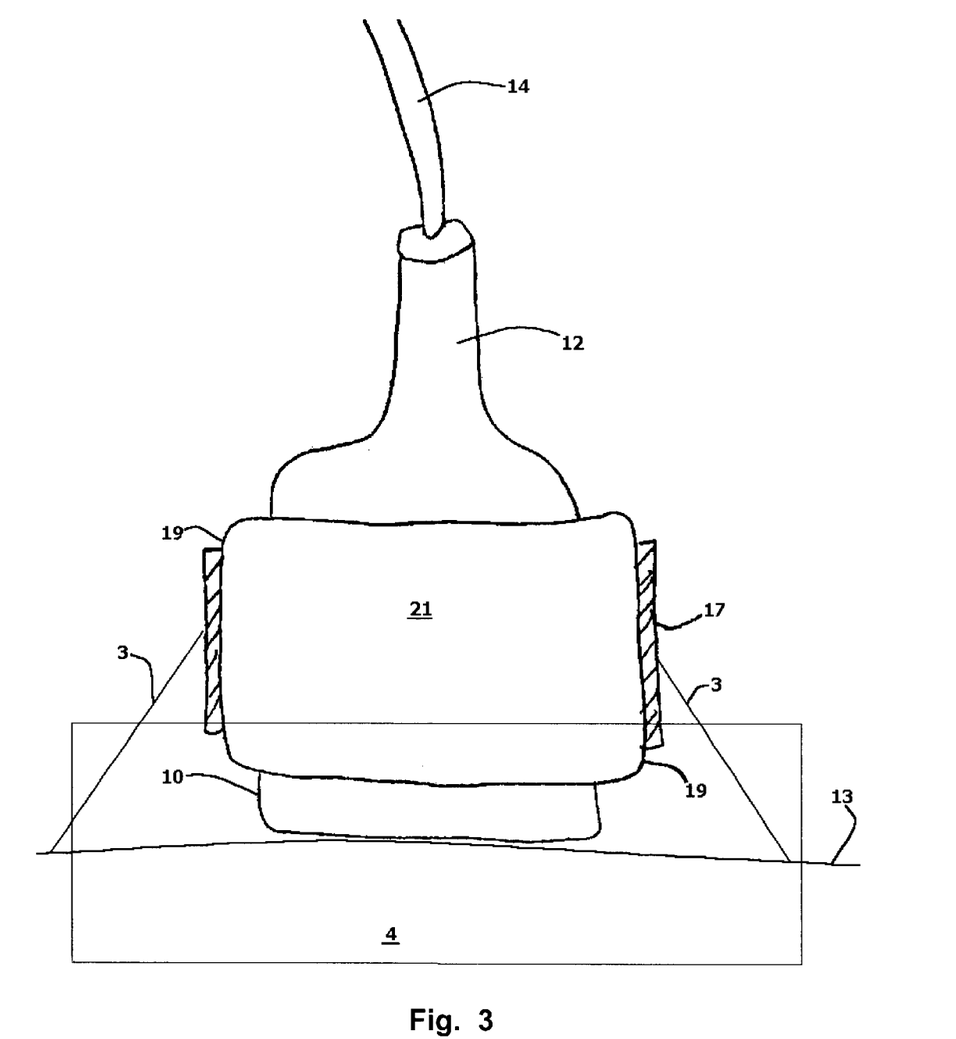
FIG. 3 is an elevation view of a second embodiment of an ultrasonic transducer and optical guide constructed according to the principles of the present invention.
Figure 4:
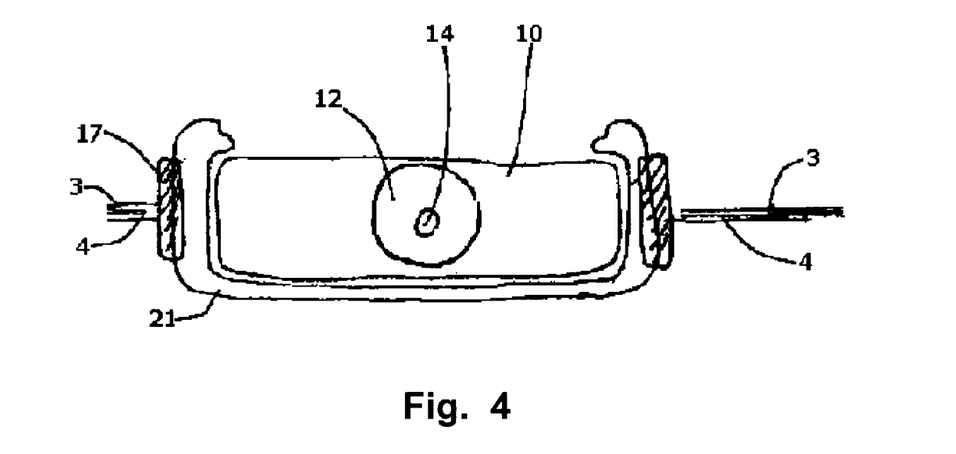
FIG. 4 is a plan view of the transducer and optical guide depicted in FIG. 3.

Referring to FIG. 3, in one alternate embodiment of the invention, the mount 16 is replaced by a clip 21 which surrounds at least a portion of transducer 10. The lateral surfaces 19 of the clip 21 serve as a base for a series of linearly arranged light emitting diodes 17. The diodes 17 can be replaced by suitable fiber optics or other light sources that will create a line 3 residing within the imaging plane 4. As seen in FIG. 4, the line 3 projected by the diodes 17 is collinear with the edge of ultrasonic imaging plane 4.

Figure 5:
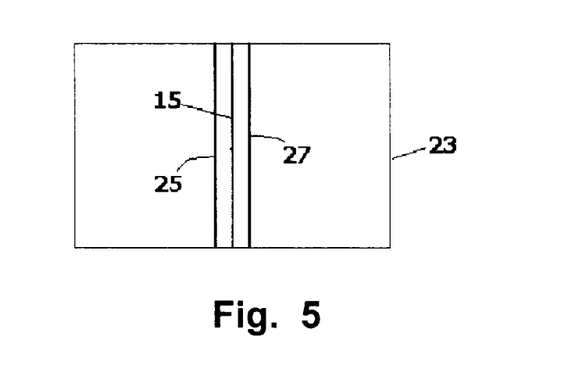
FIG. 5 is a pictorial depiction of a guide display embodying the principles of the present invention.

In another alternate embodiment of the needle guide, the light source or laser 22 is replaced by a video camera. A miniature video camera is attached to the transducer via mount 24 and oriented toward the patient 13. In particular, if the camera is of the lipstick variety, that is, has a cylindrical body, the mechanical mount 24 would only need to be adapted from the laser diameter to the diameter of the camera. The camera's optical axis is collinear with the laser beam 3 of the previous embodiment and hence lies in the ultrasound imaging plane. Referring also to FIG. 5, the ultrasound plane 4 corresponds to a line 15 appearing in the video image 23.

Ideally, the camera is aligned around its optical axis so that the line is oriented either vertically or horizontally within the video image 23. Preferably, graphical markers 25 and 27 are overlaid onto the video image 23 to bracket or define the location of the ultrasound plane line 15. The camera provides the user with an aerial view from the transducer head 10 and displays the region on the patient 13 where the needle will be inserted. Graphical markers 25 and 27 in the image 23 indicate to the user the location of the ultrasound transducer plane 4 which contains line 15.

Figure 6:
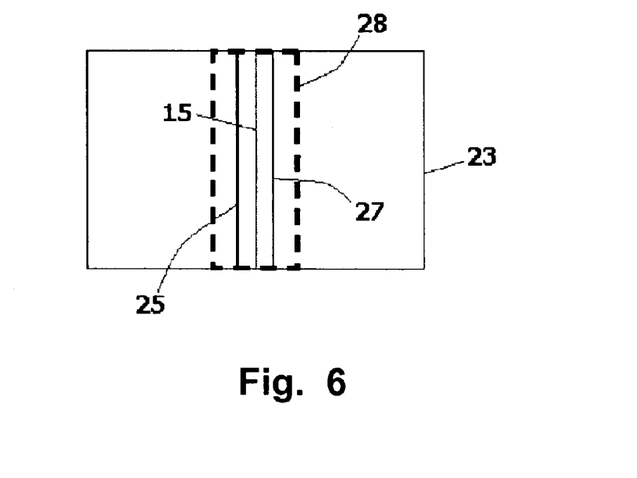
FIG. 6 is a pictorial depiction of a truncated display embodying the principles of the present invention.

The user 32 can readily choose a needle entry point that lies in the ultrasound imaging plane 4 and can further align the entire needle to lie within the plane 4, by aligning the needle as viewed in the video image 23 with the markers 15, 25 and 27 overlaid onto the video image 23. During needle insertion, the correct in-plane needle alignment can be monitored on the video image 23. The video image 23 can be displayed on a separate monitor or it can be shown as an inset on the ultrasound system's monitor 29. If the camera body has a cylindrical shape, the mount 24 may only define the orientation of the camera's vertical axis 8. In an alignment step, the camera is turned around its axis until ultrasound plane 4 corresponds to vertical or horizontal direction in the video image 23. Referring also to FIG. 6, there is no need to display the full video image 23. Rather, the user can choose to display a truncated region of interest 28 that includes the ultrasound plane line 15.

The above embodiments may also be combined with augmented reality systems which would allow the physician to see both the light beam 3 or optical image 23 with overlaid markers 25 and 27 and the patient at the same time. In addition, the ultrasonic image may also be included in the image. One such embodiment of the present invention is preferably constructed as a handheld device that includes the ultrasound transducer 10, the handle 16 for gripping the transducer 10, the light source 22 mounted to the handle 16, the flat panel monitor or display 29 and a half silvered mirror 30 linked together by mounting elements 44 and 45. The monitor or display 29, half silvered mirror 30 and transducer 10 are mechanically oriented and mounted so that the mirror 30, which is substantially planar, bisects the angle 31 formed between the transducer image plane 4 and the plane occupied by the display 29.

As long as the axis 46 of mirror 30 is perpendicular to the collinear and equal length lines 47 and 48, the user 32 perceives the reflected image 33 on the mirror 30, which is the same image 33 residing on the ultrasonic image plane 4 inside the patient 13 that is being scanned by the ultrasonic transducer 10.

When the ultrasound image 33 on the monitor 29 is positioned and scaled to preserve these geometric relationships, the user 32 will perceive the structures 34 and 35 depicted in the ultrasound image 33 as if those structures 34 and 35 were at their actual physical locations inside the patient 13. In other words, the image 33 produced by transducer 10 is projected along path 43 to the half silvered mirror, creating a composite image to the user 32 such that the image 33 appears as if it were originating along path 36, path 36 being the line of sight viewed by user 32 when observing patient 13. The pose of the user 32 is thus adapted for viewing the patient 13 rather than the monitor 29. Line of sight 36 coincides with a direct view of patient 13. Since the image 33 is an internal view of patient 13, the user 32 has the illusion of looking through the patient's skin and viewing the underlying region inside patient 13.

Since the optical effect of the half silvered mirror 30 depicts the ultrasound image 33 in the location of the actual internal structures 34, it provides natural or intuitive feedback for guidance of needle placement by the user 32. The needle is inserted towards a target 35 that can be seen in its actual physical location. However, though the user 32 can easily appreciate whether the needle points towards the target in a lateral sense, it is not so easy to see whether the needle will hit the target at the right depth. This is similar to the task of drilling a vertical hole, where it is relatively easy for the user to adjust the tilt of the drill correctly towards the left and right but it is relatively more difficult to adjust the tilt of the drill towards the front and back, that is, directly toward and away from the user. In the present invention, the optical or video guidance provided by laser beam 3 or video line 15 helps the user place the needle in the ultrasound plane 4, while the image overlay of the half silvered mirror 30 provides guidance to user 32 to adjust the tilt of the needle within the ultrasound plane 4 towards the target 35.

In case of the video guide line 15, the video image 23 is preferably displayed on the monitor 29 as an inset of the ultrasound image 33 so as to not occlude relevant information.

In one embodiment the ultrasound scanning system includes the flat panel monitor 29 mounted with the ultrasonic transducer 10 and light source 22. The ultrasonic image 33 is processed and displayed directly on monitor 29. However, if such an integrated version is not possible, a second embodiment utilizes a computer connected to the ultrasound scanning system which receives the ultrasound images 33 either in digital or in an analog format such as NTSC or PAL. In the latter version, the computer is equipped with a frame grabber or other video capture device. The computer scales and positions the ultrasound images and outputs them to the monitor 29. If the video guide line 15 is used instead of a laser beam 3, the video images are also read into the computer to be combined with the ultrasound images 33 for display on the monitor 29.

The present device can also be combined with a complete augmented reality visualization system, with which the user observes the ultrasound images and other patient data, possibly in image form, in-situ, overlaid onto her view of the patient, registered in a way that structures seen in the ultrasound images appear in the location of the actual anatomical structures. Preferably, in such a completely integrated system the user wears a head-mounted display to watch all of the available augmented images. In such an augmented reality system the video image that facilitates the in-plane needle alignment is preferably shown as an inset in the augmented images.

Figure 8:
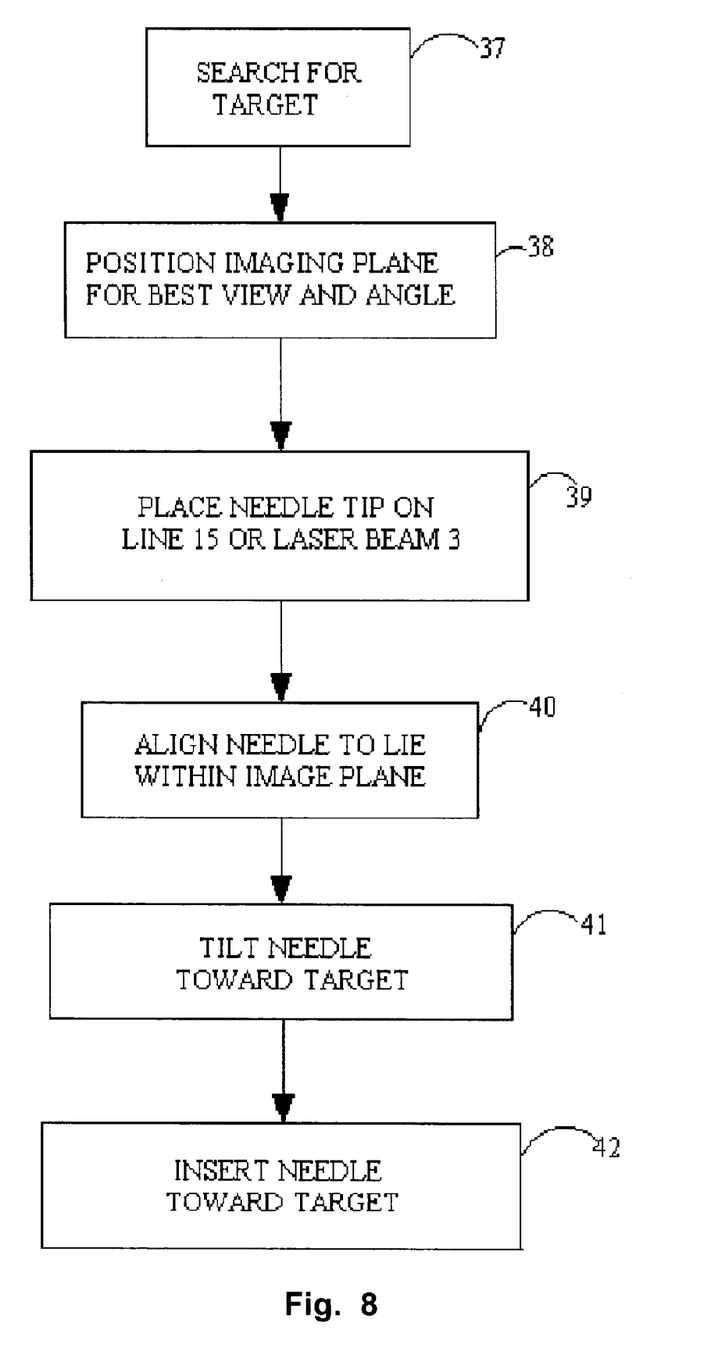
FIG. 8 is a flow chart outlining the manner of use of the device depicted in FIG. 7.

Referring also to FIG. 8, the procedure for utilizing the present invention can be better understood. At step 37, the user 32 searches for the target 35 with the transducer 10. At step 38, the user 32 brings the transducer 10 into a position where the target 35 is visible on the ultrasound image 33 and where the ultrasound plane 4 is appropriate for introducing the needle or other similar instrument into the patient 13. At step 39, the user 32 places the needle tip at an appropriate entry point on the skin surface of patient 13, guided by the light beam 3 or the video guide line 15, either of which depicts a line on the surface of the skin. By touching the needle tip to the skin at an appropriate entry point there is still no guarantee that the needle is coplanar with imaging plane 4. Rather, at the completion of step 39 the user 32 is only assured that the needle tip intersects the imaging plane 4.

At step 40, the user aligns the needle to actually lie within the ultrasound plane 4, again guided by either the laser beam 3 or the video guide line 15. This is accomplished by causing the needle to completely overlie or project onto the beam 3 or guide line 15. At step 41, the user 32 tilts the needle within the ultrasound plane 4 so as to point towards the target 35, guided by the overlaid or superimposed ultrasound image 4 and by monitoring the in-plane alignment with the optical beam 3 or the video guide line 15. Finally at step 42 the user inserts the needle towards the target 35.

What is claimed is:

1. A guide for a needle-like instrument comprising:
   an ultrasonic transducer that projects a planar ultrasound beam into an ultrasonic imaging plane beneath a surface;
   a source of illumination, aligned with the ultrasonic transducer, the source of illumination projecting a light beam onto the surface, the light beam being coplanar with the imaging plane and forming a line of light on the surface that is coincident with the ultrasonic imaging plane; and a viewing device, causing an image produced by the ultrasonic transducer to appear to be superimposed on the surface while the line of light is visible on the surface.

2. The guide of claim 1, wherein the image appearing on the viewing device is visible to a user of the guide while the user views the actual surface on which the light beam is projected.

3. The guide of claim 2, further comprising means for scaling the image produced by the ultrasonic transducer such that objects appearing in the image appear to have their actual physical dimensions.

4. The guide of claim 3, further comprising a mounting apparatus, the mounting apparatus maintaining required geometric relationships between the source of illumination, the imaging plane and the viewing device.

5. The guide of claim 4, further comprising a handle, a mounting apparatus being affixed to the handle, the handle being adapted to be manipulated by a user of the guide so as to place the ultrasonic transducer in a desired position with respect to the surface.

6. The guide of claim 5, wherein the viewing device further comprises:

a monitor, the monitor displaying the image produced by the ultrasonic transducer; and a mirror, the mirror redirecting the image to coincide with a line of sight of the user when the user is viewing the surface.

7. The guide of claim 6, wherein the mirror resides in a plane that bisects an angle formed between the imaging plane and a plane in which the monitor resides.

8. The guide of claim 7, wherein the mirror resides in a plane that is equidistant from the imaging plane and the plane in which the monitor resides.

9. The guide of claim 1, wherein the source of illumination is a laser.

10. The guide of claim 9, wherein the laser is rotatable about a lateral axis.

11. The guide of claim 1, wherein the source of illumination is formed as a series of light emitting diodes arranged so as to reside within the imaging plane.

12. The guide of claim 11, wherein the light emitting diodes are arranged in two rows positioned on opposing sides of the ultrasonic transducer.

13. An apparatus for video assisted guidance of a needle-like instrument comprising:

means for projecting a planar ultrasound beam into an ultrasonic imaging plane beneath a surface;

means for creating a video image of the surface;

means for inserting graphic markers on the video image of the surface, the graphic markers being substantially coplanar and coincident with the ultrasonic imaging plane and indicating a line of potential entry points for a needle biopsy; and means for simultaneously viewing an image produced by the ultrasonic transducer with the video image of the surface.

14. The apparatus of claim 13, wherein the image produced by the ultrasonic transducer is superimposed on the video image of the surface.

15. The apparatus of claim 14, further comprising means for reorienting the graphic markers appearing in the video image.

16. A method of inserting an instrument into a comprising the steps of:

projecting a planar ultrasound beam into an ultrasonic imaging plane into the body;

projecting a linear beam of light onto a surface of the body such that a line of light is formed on the surface and is coincident with the ultrasonic imaging plane;

deriving image information from the ultrasound transducer;

superimposing derived ultrasonic image information onto a view of the line of light appearing on the surface of the body so as to create a composite image; and viewing the composite image while inserting instrument into the body.

17. The method of claim 16, further comprising the steps of:

moving the ultrasonic transducer on the surface of the body until a desired object is visible in the derived ultrasonic image; and orienting the ultrasonic transducer such that the line of light appears at a desired location.

18. The method of claim 16, further comprising the steps of:

placing an insertable portion of the instrument on a point contained in the line of light appearing on the surface; and aligning the insertable portion of the instrument with the line of light, thereby insuring that the insertable portion of the instrument is coplanar with the imaging plane.

19. The method of claim 18, further comprising the steps of:

tilting the insertable portion of the instrument so that the insertable portion is pointed at the desired object; and advancing the insertable portion of the instrument toward the desired object.

20. The method of claim 18 wherein said step of aligning the insertable portion of the instrument further comprises the step of:

aligning the instrument with the line of light such that the instrument is illuminated along its length by the linear beam of light.

* * * * *